United States Patent
Reicher et al.

(10) Patent No.: US 10,614,570 B2
(45) Date of Patent: Apr. 7, 2020

(54) MEDICAL IMAGE EXAM NAVIGATION USING SIMULATED ANATOMICAL PHOTOGRAPHS

(71) Applicant: INTERNATIONAL BUSINESS MACHINES CORPORATION, Armonk, NY (US)

(72) Inventors: Murray A. Reicher, Rancho Santa Fe, CA (US); James G. Thompson, Escondido, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 174 days.

(21) Appl. No.: 15/849,619

(22) Filed: Dec. 20, 2017

(65) Prior Publication Data

US 2019/0188850 A1    Jun. 20, 2019

(51) Int. Cl.
| | |
|---|---|
| *G06T 7/00* | (2017.01) |
| *G06T 7/33* | (2017.01) |
| *A61B 6/00* | (2006.01) |
| *A61B 6/03* | (2006.01) |
| *G06K 9/62* | (2006.01) |

(52) U.S. Cl.
CPC .............. *G06T 7/0012* (2013.01); *A61B 6/03* (2013.01); *A61B 6/5229* (2013.01); *G06K 9/6254* (2013.01); *G06T 7/344* (2017.01); *A61B 6/5294* (2013.01); *G06K 2209/051* (2013.01); *G06K 2209/055* (2013.01); *G06T 2207/10081* (2013.01); *G06T 2207/10088* (2013.01); *G06T 2207/10104* (2013.01); *G06T 2207/10116* (2013.01); *G06T 2207/10132* (2013.01); *G06T 2207/30004* (2013.01)

(58) Field of Classification Search
CPC ......... G06T 7/0012; G06T 7/30; G06T 7/344; G06T 11/00; G06T 2200/21; G06T 2210/41; G16H 30/40; G16H 50/50; A61B 6/5229; A61B 6/5294

See application file for complete search history.

(56) References Cited

U.S. PATENT DOCUMENTS

| | | | |
|---|---|---|---|
| 7,633,501 B2 | 12/2009 | Wood et al. .................. 345/419 |
| 8,682,626 B2 | 3/2014 | Ionasec et al. .................... 703/6 |
| 9,286,673 B2 | 3/2016 | Begin et al. .......... G06T 7/0012 |
| 9,445,713 B2 | 9/2016 | Douglas et al. ........ A61B 1/227 |
| 9,600,138 B2 | 3/2017 | Thomas et al. ...... G06F 3/04815 |
| 9,760,690 B1 | 9/2017 | Petkov et al. ......... G06F 19/345 |
| 2006/0111631 A1 | 5/2006 | Kelliher et al. ................ 600/425 |
| 2008/0015418 A1 | 1/2008 | Jarrell et al. ................... 600/300 |
| 2013/0325493 A1 | 12/2013 | Wong et al. .......... G06F 19/345 |
| 2015/0051921 A1* | 2/2015 | Tran ...................... G06F 19/321 705/3 |
| 2016/0350919 A1 | 12/2016 | Steigauf et al. ....... G06T 7/0014 |
| 2016/0364862 A1 | 12/2016 | Reicher et al. ........ G06T 7/0014 |
| 2019/0090824 A1* | 3/2019 | Brunicardi ............. A61B 6/032 |

FOREIGN PATENT DOCUMENTS

WO    9959106 A1    11/1999    ............. G06T 15/00

OTHER PUBLICATIONS

Xue, Z. et al., "Body Segment Classification for Visible Human Cross Section Slices," 2014 IEEE 27th International Symposium on Computer-Based Medical Systems, 2014.
Anonymous, "Automated Classification of Computed Tomography Axial Slices into Anatomical Region Labels," IP.com; http://ip.com/IPCOM/000239810D; Dec. 3, 2014.
Anonymous, "Segmentation of Thin Anatomical Structures in Medical Imaging," IP.com; http://ip.com/IPCOM/000194368D; Mar. 22, 2010.
Anonymous, "Volume Computed Tomography Method for Anatomical Objects in Medical Imaging," IP.com; http://ip.com/IPCOM/000124113D; Apr. 8, 2005.
Hinshaw, K., "Seeing Structure: Using Knowledge to Reconstruct and Illustrate Anatomy," Dissertation, University of Washington, 2000.
Mandalika, V., et al. "A Hybrid 2D/3D User Interface for Radiological Diagnosis," Journal of Digital Imaging (2017): 1-18.
Notice of Allowance from the U.S. Patent and Trademark Office for U.S. Appl. No. 15/849,614 dated Aug. 19, 2019 (14 pages).

\* cited by examiner

*Primary Examiner* — Andrew W Johns
(74) *Attorney, Agent, or Firm* — Michael Best & Friedrich LLP

(57) ABSTRACT

Methods and systems for generating and displaying a simulated anatomical photograph. One system includes an electronic processor. The electronic processor is configured to receive a first selection from a user, the first selection designating a body part of a patient, receive a second selection from the user, the second selection designating a time period, automatically access imaging information for the patient associated with the first selection and the second selection, automatically generate the simulated anatomical photograph for the body part for the time period based on the imaging information, and display the simulated anatomical photograph to the user within a graphical user interface.

20 Claims, 9 Drawing Sheets
(7 of 9 Drawing Sheet(s) Filed in Color)

Jane Doe
BORN: 3/12/1966 (51 YRS)
SEX: OTHER
MRN: 12345
IPID: 5432176

RACE: WHITE (CAUCASIAN)
ETHNICITY: NON HISPANIC
GENDER: MALE TO FEMALE
SEXUAL ORIENT: BISEXUAL
LANGUAGE: SWEDISH (swe)

STATUS: ACTIVE
INS: ELIGIBLE

SMOKER: YES

| EXAM HISTORY | CLINICAL SUMMARY | NOTES |

FULL BODY

LEFT SHOULDER

SIMULATED

XRAY 8/12/2017 | REP    XRAY 9/17/2017 | REP

MR 9/30/2017 | REP    CT 10/5/2017 | REP

C  1D  7D     6M  1Y  3Y  MAX         2017

7/30    10/31

MEDICAL IMAGE EXAM NAVIGATION USING SIMULATED ANATOMICAL PHOTOGRAPHS

SUMMARY

Physicians (whether human or veterinary) spend significant time learning the anatomy of the human body, including working with cadavers and studying photographs taken of cadavers, including surgical slices of cadavers. Some physicians, such as radiologists and other medical imaging specialists, also spend significant time learning the physics of various medical imaging modalities and how to read and analyze images generated by such modalities using various imaging procedures and techniques. These physicians learn to interpret various imaging modalities (such as radiographs, MRI, CT, PET, ultrasound, nuclear imaging, and the like) and how the images depict human anatomy and physiology. They learn the physics of each modality and artifacts so that they can integrate the displayed information to imagine and describe the results of one or more imaging exams. They learn how to derive information from various changes in imaging conditions, such as the projections(s), use of various contrast agents, radiopharmaceuticals, MRI pulse sequences, and the like. For example, an imaging modality generates an image of a patient, but the image is in fact a pictorial representation of the patient's anatomy and sometimes physiology based on sensed data and is not directly equivalent to what the patient's anatomy would look like were a surgical slice made of the patient's tissue and photographed with a camera. In other words, medical images help specialized physicians imagine a patient's anatomy and physiology, but medical images are not the same as photographs of patient, a patient cavity, or a slice of tissue.

Accordingly, when a reading physician or other imaging specialist ("reading physician") subsequently receives a medical image study, the reading physician creates a clinical report that interprets the images included in the study based on the reading physician's understanding of how a particular imaging modality generates the pictorial representation of a patient's anatomy. Thus, the reading physician is doing more than just reporting anatomical changes but rather is drawing on an understanding of the image technique, anatomy, disease, and other information related to a patient to conclude whether a tissue is normal or abnormal, make a possible diagnosis or the like.

The reading physician often communicates these findings to other physicians and caregivers, such as a referring physician who ordered the imaging procedure. These other physicians may lack specific training in reading and analyzing medical images and, thus, may lack familiarity with the physics of the various imaging technologies, which may inhibit the physicians from directly extracting information from the medical images. Accordingly, these physicians may rely on the reading physician's explanation of the medical images.

To address these and other problems, embodiments described herein provide systems and methods for generating simulated photographic anatomical slices from images included in an image study generated by an imaging modality. As the majority of physicians are well-versed in anatomy, the simulated photographic anatomical slices convey useful information to all physicians, which may allow physicians to assist in an efficient and accurate diagnosis.

For example, the methods and systems described herein compile and convert medical images into two-dimensional or three-dimensional simulated anatomical photographs, including photographs that can be modified by the user to show various possible diagnoses and appearances at various selected times. Such systems and methods allow the training of reading physicians to be dramatically shortened, because they would not necessarily need to know all of the individual modalities and their physics. Such systems also enhance communication between physicians, caregivers, and patients. In particular, there is no way for any one person to know exactly what another person is imagining, such as when reviewing medical images. Therefore, a reading physician may develop a great understanding of the appearance and physiology of a patient's abdomen and create an appropriate imaging report or reports. However, the operating surgeon may not have the same imaginative understanding of the same patient as the reading physician. Similarly, the patient may not have the same imaginative understanding as the reading physician. By transforming medical images from one or more exams into simulated photographs, the systems and methods described herein bring collaborators to a common denominator and one that mirrors their experience in the daily world. Also, the systems and methods described herein can be used to create images that predict the appearance of a patient's body part at various times based on the collection of data from many imaging and non-imaging sources. Accordingly, the systems and methods may further be used to more efficiently and effectively use various medical resources and provide better patient care.

As described in more detail below, the systems and methods described herein use machine learning of medical images combined with anatomical atlas references to learn how to identify an anatomical structure including, optionally, its boundaries, a process commonly referred to as "anatomical segmentation." For example, the systems and methods described herein may learn to look at a magnetic resonance image (MRI) of a shoulder and identify the supraspinatus muscle and the tendon. The systems and methods may also use machine learning to learn to transform the pixels in an cross-sectional medical image to the color and shading that would appear had the depicted anatomical structure been photographed as a cross-sectional slice of tissue. For example, the systems and methods described herein may learn to convert a monochrome MM of a shoulder to an image where the supraspinatus muscle appears as it would appear in living tissue if photographed as a cross-sectional slice or viewed by a human eye under various lighting conditions. The systems and methods may use stored knowledge related to various imaging procedures, such as MRI, computed tomography (CT), Ultrasound, positron-emission tomography (PET) scans, and nuclear imaging scans. Such knowledge, which parallels what an imaging specialist learns during years of training, may inter-relate the imaging technique, imaging parameters (such as information in a Digital Imaging and Communications in Medical (DICOM) metafile or header associated with an image), body part, and depicted anatomy to derive the composition and characteristics of a particular finding, pixel, or voxel. For example, the systems and methods may learn that certain information in the DICOM metafile or in the images themselves indicates that an image is a fat-suppressed MRI, or that another image depicting the same location was obtained without fat-suppression. As a result of this data collection and knowledge, the systems and methods could determine that a pixel that is low in signal intensity on a fat suppressed image and higher in signal strength on a non-fat suppressed image represent fat or a fat-containing structure. Therefore, the systems and methods could create a simulated anatomical photograph in which that pixel is shown as fat would appear to the human eye under one or more lighting conditions.

Embodiments described herein may also provide various user interfaces, including graphical user interfaces (GUIs), that display simulated anatomical photographs to a user. In some embodiments, the (GUIs) may display confidence information for pixels (or voxels) of a SAP that indicates how confident the system is in the pixel. Accordingly, ambiguously-defined pixels (or voxels) may be clearly marked so that a user can use this information in reading and interpreting the SAP. The user may also interact with a SAP through a GUI to correct portions of a SAP, view additional data associated with the SAP (such as anatomical labels), see options for particular pixels (or voxels) (likely pixel representations given available information), supplement information that may be used to generate a SAP or a portion thereof, or the like. How SAPS are displayed to a user and manipulated by a user may also be governed by various configurable (manually or automatically) rules.

Embodiments described herein also generate and provide an improved graphical user interface for displaying simulated anatomical photographs. For example, rather than viewing traditional imaging exam timelines and sortable lists of image studies, a user can select and specify what SAPs to display, which may not be tied to a specific imaging procedure but rather may be generated based a compiled set of information (clinical information, non-clinical information, or a combination thereof). For example, instead of selecting exams from a timeline, a graphical user interface is generated that provides a graphical presentation of a body from which a user can understand what has been previously imaged and make intelligent selections to obtain needed information for a patient. Default preferences for the graphical user interface may be learned over time using artificial intelligence to improve efficiency and use of the available information.

For example, some embodiments described herein provide a method of generating a simulated anatomical photograph based on a medical image generated by an imaging modality. The method includes receiving, with an electronic processor, the medical image, anatomically segmenting the medical image, with the electronic processor, to determine a plurality of anatomical structures represented in the medical image, determining, with the electronic processor, how each of the plurality of anatomical structures is photographically depicted by accessing at least one knowledge base, and generating, with the electronic processor, the simulated anatomical photograph based on the plurality of anatomical structures and how each of the plurality of anatomical structures is photographically depicted. The pixels of the simulated anatomical photograph representing a simulated cross-sectional anatomical photograph of the plurality of anatomical structures. The method also includes displaying, with the electronic processor via a display device, the simulated anatomical photograph within a user interface.

Another embodiment provides a system for generating a simulated anatomical photograph based on a medical image generated by an imaging modality. The system includes an electronic processor. The electronic processor is configured to receive the medical image, anatomically segment the medical image to determine a plurality of anatomical structures represented in the medical image, determine how each of the plurality of anatomical structures is photographically depicted by accessing at least one knowledge base, and generate the simulated anatomical photograph based on the plurality of anatomical structures and how each of the plurality of anatomical structures is photographically depicted. The pixels of the simulated anatomical photograph representing a simulated cross-sectional anatomical photograph of the plurality of anatomical structures. The electronic processor is also configured to display, via a display device, the simulated anatomical photograph within a user interface.

Yet another embodiment provides non-transitory computer-readable medium storing instructions that, when executed by an electronic processor, perform a set of functions. The set of functions comprising receiving a medical image generated by an imaging modality, anatomically segmenting the medical image to determine a plurality of anatomical structures represented in the medical image, determining how each of the plurality of anatomical structures is photographically depicted by accessing at least one knowledge base, and generating the simulated anatomical photograph based on the plurality of anatomical structures and how each of the plurality of anatomical structures is photographically depicted. The pixels of the simulated anatomical photograph representing a simulated cross-sectional anatomical photograph of the plurality of anatomical structures. The set of functions further includes displaying, via a display device, the simulated anatomical photograph within a user interface.

A further embodiment provides a system for generating and displaying a simulated anatomical photograph based on a medical image generated by an imaging modality. The system includes an electronic processor. The electronic processor is configured to receive the medical image, determine an anatomical structure in the medical image, and automatically generate the simulated anatomical photograph based on the anatomical structure. The pixels of the simulated anatomical photograph represent a simulated cross-sectional anatomical photograph of the anatomical structure. The electronic processor is also configured to determine a degree of confidence of a portion of the simulated anatomical photograph, compare the degree of confidence to a threshold, and, in response to the degree of confidence of the portion of the simulated anatomical photograph failing to satisfy the threshold, display the portion of the simulated anatomical photograph differently from another portion of the simulated anatomical photograph.

Another embodiment provides a method of generating and displaying a simulated anatomical photograph based on a medical image generated by an imaging modality. The method includes receiving, with an electronic processor, the medical image, determining, with the electronic processor, an anatomical structure for each of a plurality of pixels included in the medical image, determining, with the electronic processor, a degree of confidence of the anatomical structure determined for each of the plurality of pixels included in the medical image, and automatically, with the electronic processor, transforming each of the plurality of pixels in the medical image based on the anatomical structure determined for the pixel to generate the simulated anatomical photograph. The simulated anatomical photograph representing a simulated cross-sectional anatomical photograph of the anatomical structure determined for each of the plurality of pixels included in the medical image. The method also includes comparing, with the electronic processor, the degree of confidence of the anatomical structure determined for each of the plurality of pixels included in the medical image with a configurable threshold, and, in response to the degree of confidence for a pixel in the plurality of pixels not satisfying the threshold, displaying the pixel differently than a pixel in the plurality of pixels satisfying the threshold.

Yet another embodiment provides non-transitory computer-readable medium storing instructions that, when executed by an electronic processor, perform a set of functions. The set of functions comprising receiving a medical image generated by an imaging modality, determining an anatomical structure for each of a plurality of pixels included in the medical image, determining a degree of confidence of the anatomical structure determined for each of the plurality of pixels, and automatically transforming each of the plurality of pixels based on the anatomical structure determined for the pixel to generate the simulated anatomical photograph. The simulated anatomical photograph representing a simulated cross-sectional anatomical photograph of the anatomical structure determined for each of the plurality of pixels. The set of functions further comprising comparing the degree of confidence of the anatomical structure determined for each of the plurality of pixels with a configurable threshold, and, in response to the degree of confidence for a pixel in the plurality of pixels not satisfying the threshold, displaying the pixel differently than a pixel in the plurality of pixels satisfying the threshold based on at least one user preference.

Still another embodiment provides a system for generating and displaying a simulated anatomical photograph. The system includes an electronic processor. The electronic processor is configured to receive a first selection from a user, the first selection designating a body part of a patient, receive a second selection from the user, the second selection designating a time period, automatically access imaging information for the patient associated with the first selection and the second selection, automatically generate the simulated anatomical photograph for the body part for the time period based on the imaging information, and display the simulated anatomical photograph to the user within a graphical user interface.

Still a further embodiment provides a method of generating and displaying a simulated anatomical photograph. The method includes receiving, with an electronic processor, a first selection from a user within a graphical user interface, the first selection designating a body part of a patient by selecting a selectable portion of a graphical representation of a body included in the graphical user interface and receiving, with the electronic processor, a second selection from the user, the second selection designating a time period. The method also includes automatically accessing, with the electronic processor, imaging information for the patient associated with the first selection and the second selection, automatically generating, with the electronic processor, the simulated anatomical photograph for the body part for the time period based on the imaging information, wherein the simulated anatomical photograph estimates an appearance of the body part for the time period in a cross-sectional anatomical slice, and displaying the simulated anatomical photograph to the user within the graphical user interface.

Another embodiment provides non-transitory computer-readable medium storing instructions that, when executed with an electronic processor, perform a set of functions. The set of functions comprising receiving a first selection from a user, the first selection designating a body part of a patient, receiving a second selection from the user, the second selection designating a time period, and automatically accessing imaging information for the patient associated with the first selection and the second selection and non-imaging information for the patient associated with the first selection and the second selection. The set of functions further includes automatically generating a simulated anatomical photograph for the body part for the time period based on the imaging information and non-imaging information, wherein the simulated anatomical photograph estimates an appearance of the body part for the time period in a cross-sectional anatomical slice, and displaying the simulated anatomical photograph to the user within the graphical user interface.

Other aspects of the invention will become apparent by consideration of the detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

Figure 1:
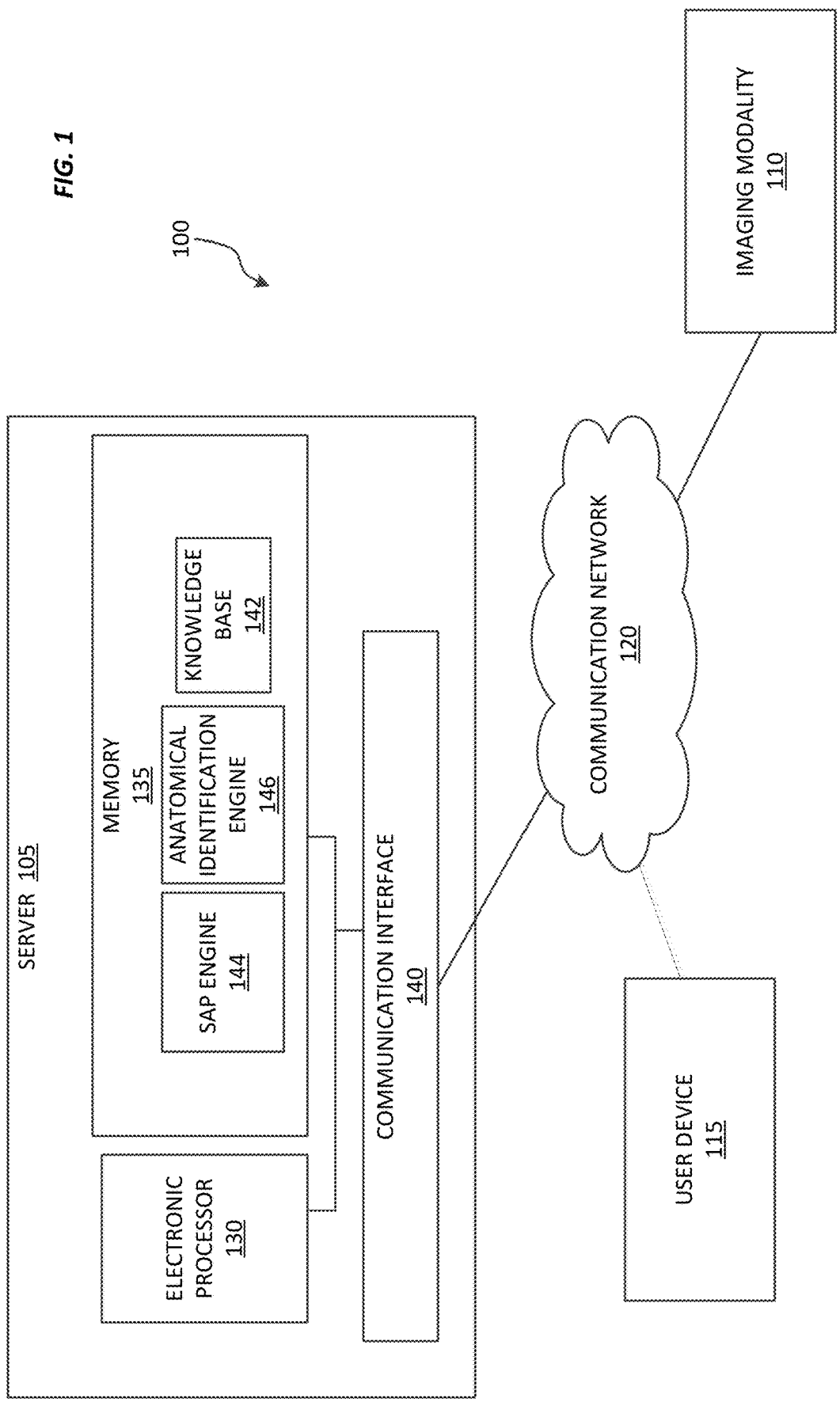
FIG. 1 illustrates a system for generating a simulated anatomical photograph according to some embodiments.

FIG. 1 illustrates a system 100 for generating simulated photographic anatomical slices (also referred to herein as SAPs). The system 100 includes a server 105, an imaging modality 110, and a user device 115. As shown in FIG. 1, the server 105, the imaging modality 110, and the user device 115 communicate over a communication network 120. It should be understood that FIG. 1 illustrates one example of the system 100, and, in some embodiments, the system 100 includes fewer or additional components in various configuration that differ from the configuration illustrated in FIG. 1. For example, in some embodiments, the system 100 includes multiple user devices 115, multiple servers 105 (such as a set of servers included in a cloud service or environment), multiple imaging modalities 110, or a combination thereof. Also, in some embodiments, the system 100 includes one or more intermediary devices. For example, the server 105 may be configured to communicate with the imaging modality 110 through a gateway or separate server, such as a picture archiving and communication system (PACS) server. However, in other embodiments, the server 105 may include a PACS server.

The imaging modality 110 generates medical images, which are accessible to the server 105. For example, the imaging modality 110 may include an MRI machine, an X-ray machine, an ultrasound machine, a CT machine, a PET machine, nuclear imaging machine, and the like. In some embodiments, the imaging modality generates medical images and forwards the medical images to the server 105. In other embodiments, the imaging modality 110 may locally store generated medical images (for subsequent retrieval or access by the server 105). In still other embodiments, the imaging modality 110 may transmit generated medical images to one or more image repositories for storage (and subsequent retrieval or access by the server 105. As noted above, in some embodiments, one or more intermediary devices may handle images generated by the imaging modality 110. For example, images generated by the imaging modality 110 may be transmitted to a medical image ordering system (including, for example, information about each medical procedure), a PACS, a radiology information system (RIS), an electronic medical record (EMR), a hospital information system (HIS), and the like.

The user device 115 may be, for example, a workstation, a personal computing device, a laptop computer, a desktop computer, a thin-client terminal, a tablet computer, a smart telephone, a smart watch or other smart wearable, or other electronic devices. In some embodiments, the user device 115 may be used to access images generated by the imaging modality 110, such as through the server 105. For example, in some embodiments, the user device 115 (an electronic processor included in the user device 115) executes a browser application or a dedicated viewing application to access one or more medical images from the imaging modality 110, the server 105, a separate image repository or image management system, or a combination thereof. Although not illustrated in FIG. 1, the user device 115 may include similar components as the server 105 (an electronic processor, a memory, and a communication interface). The user device 115 may also include one or more human machine interfaces for interacting with a user, such as, for example, a touchscreen, a keyboard, a cursor-control device (for example, a mouse, a touchpad, and the like), one or more button, a microphone, a speaker, a display (for example, a liquid crystal display (LCD), or the like. For example, in some embodiments, the user device 115 includes a display configured to display graphical user interfaces that allow a user to request a medical image, view a medical image (including a simulated anatomical photograph generated for an image as described herein), manipulate an image, and, optionally, generate a clinical report for the image or a set of images.

As illustrated in FIG. 1, the server 105 includes an electronic processor 130, a memory 135, and a communication interface 140. The electronic processor 130, the memory 135, and the communication interface 140 communicate over one or more connections or buses. The server 105 also includes other electrical and electronic components (not illustrated) that provide power, operational control, and protection of the components. It should also be understood that, in some embodiments, the server 105 includes additional components in various configurations than the example configuration illustrated in FIG. 1. For example, in some embodiments, the server 105 includes multiple memories, electronic processors, and the like.

The electronic processor 130 may be implemented as, for example, a microprocessor, an application-specific integrated circuit (ASIC), or another suitable electronic device. The electronic processor 130 accesses and executes instructions stores in the memory 135. The electronic processor 130 also receives information from the communication interface 140 and controls the communication interface 140 to transmit information to other components of the system 100. The memory 135 includes non-transitory computer-readable medium, for example, read-only memory (ROM), random access memory (RAM), electrically erasable programmable read-only memory (EEPROM), flash memory, a hard disk, a secure digital (SD) card, other suitable memory devices, or a combination thereof. The memory 135 stores computer-readable instructions ("software") executed by the electronic processor 130. The software may include firmware, one or more applications, program data, filters, rules, one or more program modules, and other executable instructions. For example, the software may include instructions and associated data for performing the methods described below.

In particular, as shown in FIG. 1, the memory 135 stores a knowledge base 142, a SAP engine 144, and an anatomical identification engine 146. It should be understood that the software components illustrated in FIG. 1 and described herein can be combined and distributed in various configurations. For example, in some embodiments, the functionality described herein as being performed by the SAP engine 144, the anatomical identification engine 146, or both may be distributed among multiple software components. Similarly, in some embodiments, the memory 135 may store a single software component that performs the functionality of the SAP engine 144 and the anatomical identification engine 146. Also, in some embodiments, the server 105 may access the functionality provided by the SAP engine 144, the anatomical identification engine 146, or both through one or more application programming interfaces (APIs). In addition, in some embodiments, the knowledge base 142 may be distributed over multiple memory modules included in the server 105, external to the server 105, or a combination thereof The knowledge base 142 stores (or is developed from) information about one or more imaging modalities (for example, MRI, CT, and others), including data imaging physics and artifacts and techniques used to perform various types of imaging exams or procedures (for example, uses of contrast agents). For example, the knowledge base 142 may be developed using deep learning to understand that a particular imaging artifact (such as through transmission of an ultrasound beam or other type of imaging source used in an imaging modality) is associated with a particular object, such as a tissue, a bone, a cyst, a tumor, fat, and the like. Accordingly, the knowledge base 142 may "see" the effects of transmission of various beams or other imaging sources without actually knowing the physics behind a particular imaging source. The knowledge base 142 also stores information regarding characteristics of one or more parts of anatomy represented in photographic images (slices). For example, the knowledge base 142 may store information regarding the color, contrast, brightness, etc. of a particular anatomical structure when represented in a photographic image (such as of a cadaver or surgical patient). In some embodiments, this information is stored as actual photographic images, wherein pixels or groups of pixels within the images are labeled with identifiers of the piece of anatomy represented in the images. For example, a pixel in a photographic image may be labeled with an identifier that indicates whether a pixel corresponds to fat, a particular muscle, a blood vessel, a tendon, a cyst, a kidney stone, and the like. In some embodiments, the data regarding characteristics of parts of anatomy stored in the knowledge base 142 are also associated with patient demographic information. For example, the knowledge base 142 may store a color of a particular muscle in a male patient, a female, patient, a smoker, a non-smoker, a child, and the like. As described in more detail below, the SAP engine 144 (as executed by the electronic processor 130) may access data in the knowledge base to translate a medical image generated by the imaging modality to a SAP. Also, in some embodiments, the knowledge base 142 may be distributed among multiple knowledge bases, including linked databases, layered databases, or the like. For example, there might be one knowledge base used to anatomically segment images or perhaps one knowledge base for each imaging modality or body part. Similarly, there might be another knowledge base that determines how each normal structure should look when depicted in a simulated photograph. There could be another knowledge base that is used to look for tubular structures that have imaging characteristics indicating arteries versus veins versus lymphatics versus ducts. There could also be another knowledge base that is used to find tumors, bleeds, or other anomalies. There could be another knowledge base that is used to deduce various possible causes of an ambiguous pixel (a high density pixel could be blood, calcium, talc, or the like and present various choices. There could be another knowledge base that is used to deduce a possible histology (for example, lung adenocarcinoma) based on imaging information. Accordingly, while there could be one knowledge base, there will likely be many knowledge bases or associated engines working together to turn one or more medical images from one or many exams into a SAP.

The electronic processor 130 executes the SAP engine 144 to generate a SAP as described in more detail below with respect to FIG. 2. Similarly, the electronic processor 130 executes the anatomical identification engine 146 to identify an anatomical structure within a medical image as described in more detail with respect to FIG. 2. In some embodiments, the engine 144, the engine 146, or a combination thereof uses models developed using various machine learning techniques. Machine learning generally refers to the ability of a computer program to learn without being explicitly programmed. In some embodiments, a computer program is configured to construct a model (for example, one or more algorithms) based on example inputs. Supervised learning involves presenting a computer program with example inputs and their desired (for example, actual) outputs. The computer program is configured to learn a general rule (for example, a model) that maps the inputs to the outputs. The computer program may be configured to perform deep machine learning using various types of methods and mechanisms. For example, the computer program may perform deep machine learning using decision tree learning, association rule learning, artificial neural networks, inductive logic programming, support vector machines, clustering, Bayesian networks, reinforcement learning, representation learning, similarity and metric learning, sparse dictionary learning, and genetic algorithms. Using all of these approaches, a computer program may ingest, parse, and understand data and progressively refine models for data analytics. Accordingly, using machine learning, a computer system can exceed human performance in certain tasks such as registration of images or processing multiple simultaneous variables.

The communication interface 140 enables the server 105 to communicate with the user device 115 and the imaging modality 110. In some embodiments, the communication interface 140 may be a wired interface and include, for example, a port to communicate with the imaging modality 110, the user device 115, or both. In some embodiments, the communication interface 140 may be a wireless interface and include, for example, a transceiver for establishing a wireless connection with the imaging modality 110, the user device 115, or both. The transceiver may communicate, for example, over the communication network 120. The communication network 120 may include a local area network ("LAN"), a wide area network ("WAN"), the Internet, or the like.

Figure 2:
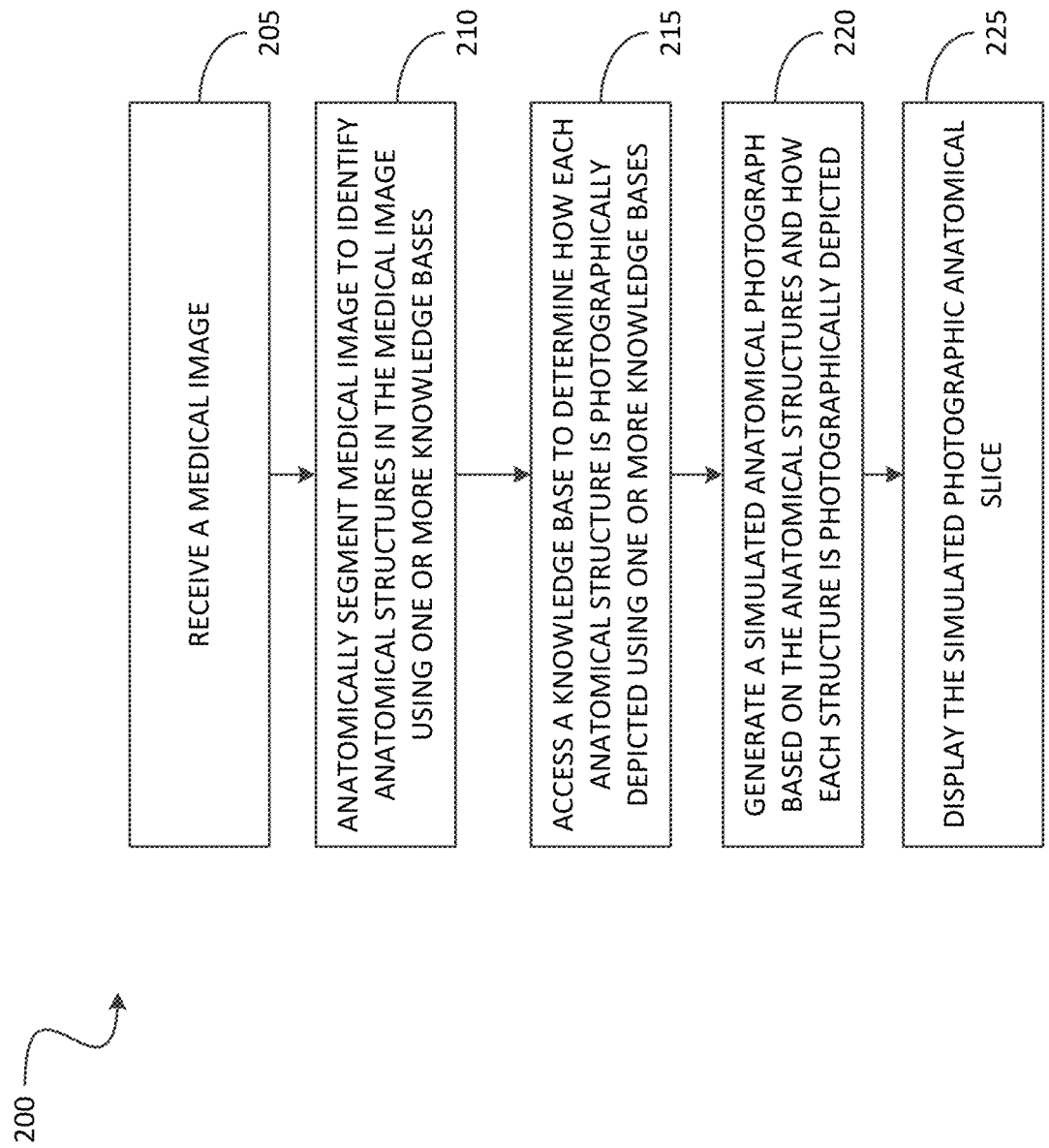
FIG. 2 is a flowchart illustrating a method of generating a simulated anatomical photographic performed by the system of FIG. 1 according to some embodiments.

FIG. 2 is a flowchart illustrating a method 200 of generating a simulated photographic anatomical slice performed by the system 100. The method 200 is described as being performed by the server 105 and, in particular, by the electronic processor 130 executing software, such as the SAP engine 144. However, it should be understood that the functionality described below with respect to the method 200 (or a portion thereof) may be performed by other components, including, for example, the user device 115 and the imaging modality 110.

As illustrated in FIG. 2, the method 200 includes receiving, with the electronic processor 130, a medical image generated by the imaging modality 110 (at block 205). As noted above, in some embodiments, the imaging modality 110 may transmit a medical image to the server 105 in response to performing or completing an imaging exam or procedure. In another embodiment, the electronic processor 130 receives the medical image (from the imaging modality or another source) in response to receiving a request from the user device 115 for a specific medical image or medical image study. As also noted above, in some embodiments, the electronic processor 130 accesses a medical image stored in an image repository, such as via a PACS server.

The method 200 also includes anatomically segmenting the medical image to determine a plurality of anatomical structures represented in the medical image (at block 210). An anatomical structure refers to a part of a body such as, for example, an organs, tissue (for example, a muscle), bones, or cells or group of cells (for example, tumors, cysts, and the like). In some embodiments, an anatomical structure is determined for individual pixels of the medical image. In other embodiments, an anatomical structure is determined for a group of pixels representing a portion of the medical image. Accordingly, in some embodiments, multiple anatomical structures are determined for a medical image and, in some embodiments, a single anatomical structure is defined for each pixel of a plurality of pixels included in a medical image. In some embodiments, an anatomical structure is determined for each pixel included in a medical image. However, in other embodiments, an anatomical structure is determined for less than all of the pixels included in a medical image, such as to focus on particular anatomical structures, control processing speed or desired SAP quality, or the like.

In some embodiments, the electronic processor 130 determines the anatomical structures based on input from a user. For example, after receiving the medical image, the medical image may be displayed (via a display of the user device 115) to a user, and the user may designate one or more anatomical structures represented in the medical image.

Alternatively or in addition, the electronic processor 130 may determine the anatomical structures automatically. For example, the electronic processor 130 may execute the anatomical identification engine 146 to automatically determine the anatomical structures. The anatomical identification engine 146 may segment the medical image into multiple segments and determine an anatomical structure in each or a plurality of segments by automatically identifying artifacts, such as predetermined patterns, shapes, or the like. In some embodiments, the anatomical identification engine 146 uses information stored in the knowledge base 142 to identify the anatomical structures in the medical image. For example, the anatomical identification engine 136 may use information regarding how a particular structure appears in particular images generated by particular imaging modalities for particular types of imaging procedures and techniques to automatically identify anatomical structures in the medical image. In particular, the knowledge base 142 may store information that indicates that the imaging modality 110 generates images where dense structures, such as bones, are represented with light (white) pixels or artifacts and less dense structures, such as fluid-filled vessels are represented with darker (black or grey) pixels or artifacts. Similarly, in some embodiments, the knowledge base 142 may store information used to integrate an array of features (including the density, shape, orientation, or more complex characteristics (contrast enhancement, fat suppression, flow, and the like) to determine what a particular segment of an image actually represents anatomically. Accordingly, the anatomical identification engine 146 may use metadata associated with the received medical image or analysis of the images themselves, such as data regarding the imaging modality 110 and the imaging procedure and technique used, to automatically identify and segment anatomical structures within the image. It may then apply conclusions about the segmented normal and abnormal anatomy along with knowledge about how that anatomy or anomaly might appear to the human eye under various lighting conditions to create a simulated anatomical photograph in two or even three dimensions, and may even add overlays to the simulations to depict things like flow, metabolic (glucose metabolism), or physiologic information that may also be available or derived from the images or metafiles that a human eye may not otherwise be able to see in a picture alone.

In some embodiments, the electronic processor 130 implements a series of image preprocessing techniques on the received medical image before determining anatomical structures in the image. For example, the electronic processor 130 may resize the medical image, segment the medical image, register the medical image with other images, or the like. For example, the electronic processor 130 may register cross-sectional medical images obtained from the same patient at different times, with the same or different imaging modalities. The electronic processor 130 may then be able to identify a particular set of pixels based on more than one medical image. For example, the electronic processor 130 may be configured to compare two or more imaging exams of a patient (for example, an MRI showing a focus of low signal intensity and a CT of the same location showing very high density) to determine an anatomical structure in the received medical image. The images compared by the electronic processor 130 may use the same or different imaging procedures.

As noted above, in some embodiments, the anatomical identification engine 146 is trained using various machine learning techniques to develop models for identifying anatomical structures. For example, by training the anatomical identification engine 146 with medical images labeled with known anatomical structures, the anatomical identification engine 146 can automatically build models that can be used to automatically identify structures is unlabeled medical images.

As illustrated in FIG. 2, the method also includes determining, with the electronic processor, how each of the plurality of anatomical structures is photographically depicted by accessing at least one knowledge base, such as the knowledge base 142 (at block 215). For example, as described above, the knowledge base 142 may store pixel characteristics of how various anatomical structures are depicted in actual anatomical photographs (or to a human eye). In some embodiments, this information is associated with patient demographics. In particular, the knowledge base 142 may store information regarding how a vein is photographically depicted for a child, an adult male, an adult female, a smoker, a non-smoker, and the like.

Figure 3:
FIG. 3 illustrates an example medical image generated by an imaging modality.
Figure 4:
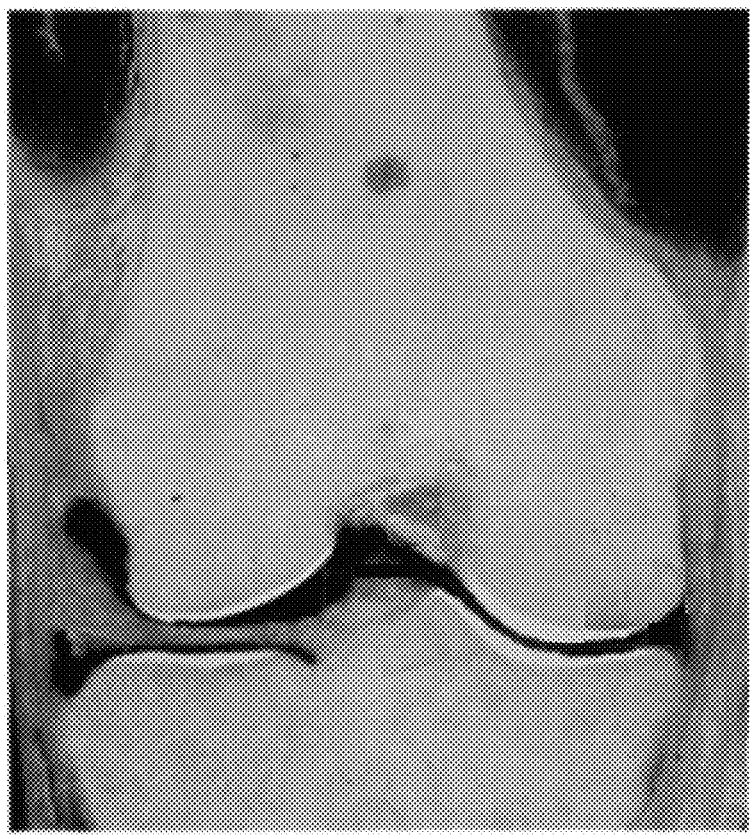
FIG. 4 illustrates an example simulated anatomical photographic generated based on the medical image of FIG. 3

As illustrated in FIG. 2, the method 200 also includes automatically generating the simulated anatomical photograph based on the plurality of anatomical structures and how each of the plurality of anatomical structures is photographically depicted, wherein the pixels of the simulated anatomical photograph represent a simulated cross-sectional anatomical photograph of the plurality of anatomical structures (at block 220) and displaying, via a display device included in the user device 115, the simulated anatomical photograph within a user interface (at block 225). For example, FIG. 4 illustrates an exemplary SAP generated based on the example medical image of FIG. 3. In particular, FIG. 4 illustrates the supraspinatus muscle of the shoulder as if it had been photographed in living tissue. In other words, the electronic processor 130 transforms the pixels in the cross-sectional medical image to the color and shading that they would appear in an anatomical photograph (for example, if the anatomical structure had been capture in photograph generated by a camera).

The electronic processor 130 may execute the SAP engine 144 to generate the SAP. The SAP engine 144 (as executed by the electronic processor 130) is configured to translate or convert pixels of the received medical image into the SAP based on knowing (i) what anatomical structures are represented in the medical image and (ii) what such anatomical structure typically look like in anatomical photos based on the data stored in the knowledge base 142. For example, based on knowing what structures are represented in a particular medical image (and where such structures are located) and what such structures look like in true anatomical photographs, SAP engine 144 can automatically transform or represent a pixel in the received medical image as the pixel would appear in an anatomical photograph. It should be understood that the SAP engine 144 may perform a pixel-by-pixel transformation, structure-by-structure transformation, or a combination thereof. Also, the SAP engine 144 may take patient information, such as patient demographics, into account when generating the SAP. For example, as noted above, the knowledge base 142 may store information about anatomical photographs associated with different types of patients, such as a female patient, a male patient, a patient with a particular disease, a patient of a particular age, and the like. Accordingly, the SAP engine 144 may be configured to transform the medical image of a patient to a SAP that best represents what the patient's true anatomical structures would look like in a photograph given the patient's demographics.

As noted above, in some embodiments, the SAP engine 144 is trained using various machine learning techniques to develop models for generating SAPs. For example, by training the anatomical identification engine 146 with SAPs generated (for example, manually or semi-automatically) for different types of medical images, true anatomical photographs, or a combination thereof, the SAP engine 144 can automatically build models that can be used to automatically generate SAP for other medical images.

For example, the SAP engine 144, the anatomical identification engine 146, or a combination thereof may learn via stored data or dynamically-learned experience that an anechoic structure on an ultrasound with sharp borders and posterior acoustic enhancement is a simple cyst. The engines 144, 146 may similarly learn that the posterior acoustic shadowing represents a blind spot on a medical image that should not be depicted as tissue on a corresponding photographic simulation of the tissue. The engines 144, 146 may also learn that increased pixel intensity in a particular location on a CT or MRI image performed after contrast injection compared to the same location imaged prior to contrast injection means that the pixel is showing contrast enhancement. The engines 144, 146 may also learn that a tubular linear or curvilinear structure with such characteristics most likely represents a blood vessel. In short, by using information about a particular imaging modality plus anatomical localization information, the system 100 may learn using artificial intelligence to create a SAP from one or more medical images.

In some embodiments, after the user device 115 displays the SAP generated by the electronic processor 130, the electronic processor 130 may receive input from a user indicating that a particular portion of the SAP is misrepresented. A user may select a particular portion of the displayed SAP by clicking on one or more pixels, circling one or more pixels, hovering over one or more pixels, speech input, or the like. In some embodiments, the user input also specifies a corrected anatomical label for the selected portion. For example, the user input may specify that the selected portion of the SAP corresponds to a muscle. The electronic processor 130 may use the feedback from the user to alter the SAP, such as based on the anatomical label received from the user. The electronic processor 130 may alter the SAP by generating a new (second) SAP that is updated based on the anatomical label received from the user. This feedback from a user may also be used to automatically update any models generated using artificial intelligence that are used to determine anatomical structures or generate a SAP.

Similarly, in some embodiments, the user interface displaying the SAP allows a user to modify the SAP by manually altering specific pixels or adding annotations. For example, in some embodiments, the user may have access to histologies, anatomical descriptions, or implanted devices that the user may use to label a medical image or label the SAP generated based on the medical image. In some embodiments, as a user modifies the SAP or the original medical image, the electronic processor 130 may be configured to automatically and dynamically update or modify the SAP. For example, in response to a user indicating that a portion of an original medical image corresponds to a pacemaker, the electronic processor 130 may automatically alter the corresponding SAP.

In some embodiments, when the electronic processor 130 determines that a portion of the medical image may correspond to two or more different anatomical structures (for example, the electronic processor 130 identifies a portion of the medical image as either a tumor or a cyst), the electronic processor 130 may generate multiple SAPs, such as a SAP for each potential anatomical structure. For example, an anatomical structure that is low in signal density on a particular MRI image may represent calcium or rapidly flowing blood. Accordingly, in this situation, the electronic processor 130 may be configured to generate a first SAP depicting the anatomical structure as calcium and generate a second SAP depicting the anatomical structure as rapidly flowing blood. In some embodiments, the electronic processor 130 may receive a user input selecting one of the SAPs. The electronic processor 130 may then store the anatomical labels associated with the selected SAP and command the user device 115 to display only the selected SAP.

Similarly, in some embodiments, the electronic processor 130 is configured to determine a degree of confidence or certainty in an anatomical structure detected in an image or a portion of a generated SAP, such as individual pixels. Thus, the electronic processor 130 may be configured to mark portions (pixels) of a SAP that have a low degree of confidence (portions with a degree of confidence failing to satisfy a user-configurable threshold). Accordingly, when reviewing a SAP, a user may receive a clear indication of what portions of a SAP are potentially less accurate than other portions. For example, the electronic processor 130 may be configured to generate a SAP illustrating anatomical slices or volumetric reconstructions with certain pixels or voxels appearing with different colors or different shading to inform the users which pixels or voxels are shown as simulated photographs and for which there is insufficient information to display a simulated photograph. Similarly, a portion of a SAP may be illustrated as a blank portion (white pixels) when the portion fails to satisfy the confidence threshold. As another example, an overlay may be provided for a SAP wherein a characteristic of the overlap (for example, a brightness, a contrast, a color, a transparency, and the like) may be varied based on the degree of confidence associated with the underlying portion of the SAP. Accordingly, portions or pixels of a SAP satisfying the threshold may be displayed differently than portions or pixels of a SAP not satisfying the threshold.

The electronic processor 130 may also request input or confirmation from a user for such portions to improve the confidence score or may automatically modify a generated SAP based on input received from a user. For example, the electronic processor 130 may be configured to access at least one clinical information source (for example, other imaging exams for the patient) (automatically or in response to user input requesting the access and, in some embodiments, designating the source) and use the accessed clinical information source to modify the SAP and improve the confidence scores. Other ways that users can interact with SAPs and modify SAPs include adjusting a SAP confidence thresholds and view a regenerated image (a threshold for how confident the system 100 needs to be in the simulated photographs appearance to display as a pixel in a simulated photograph versus some other depiction), selecting one or more sources to enable the system 100 to fill in more SAP pixels and voxels, asking the system 100 to display completely or partially filled in SAPs based on probabilities (for example, show me the most likely complete SAP for this image or exam, then show me the three most likely other options), selecting a pixel or portion of an image to cause the display to show a text description of the most likely appearance of the selected area (for example, "Most likely: 1. Blood 2. Calcification 3. High density artifact), selecting a pixel or portion of an image to cause the display to visually show various SAP options based on likely probable simulated photographic appearance of the image, allowing the user to select one of the text options (such as blood) or one of the visually displayed options to cause the SAP to be updated according to the selection, providing more clinical information to cause the SAP to be appropriately updated (for example, this patient had trauma), and editing an image to correct a SAP. As noted above, this input and interaction with a user can be provided via a speech input or command, conversational computing, a graphical user interface (including selections and annotations or other graphical inputs), or a combination thereof. In some embodiments, default display or presentation options may be defined for SAPs and how to handle low confidence scores. However, these default options may be overridden by user preferences, which as described above, may be automatically generated using various machine learning techniques.

In addition to illustrating how a patient's anatomy would appear in a cross-section anatomical photograph, the SAP may represent additional information. For example, if a user selects a pixel or group of pixels within a SAP, the user interface displaying the SAP may display anatomical label associated with the user's selection. In some embodiments, the anatomical label may be overlaid on the SAP. In some embodiments, an overlay or a dynamic label provides user with information regarding the known histology of a lesion. In some embodiments, the SAP also includes an overlaid image that provides a user with information regarding contrast enhancement, isotope uptake, flow, pallor, inflammation, or other such imaging characteristics.

In some embodiments, the electronic processor 130 generates a SAP based on one or more preferences. The preferences may be for a particular user or a group of users. The preferences may relate to, for example, whether and which SAPs are generated and displayed based on, for example, patient demographics, medical conditions, risk factors, exam type, body part, imaging modality, user role, specific user, location of service, or similar information. For example, the preferences may indicate, for example, whether a SAP is displayed instead of or in addition to a medical image. In some embodiments, the server 105 may be configured to track user activities to initially generate user preferences or update existing preferences to improve the preferences and system automation over time.

Thus, the invention provides, among other things, systems and methods for depicted cross-sectional medical images captured by various type of imaging modalities to simulated anatomical photographs so that physicians who read medical images and other, including referrers and patients, no longer need to understand the physics of various imaging modalities when viewing medical images. As described above, the systems and methods use image analytics, artificial intelligence, a medical imaging-related knowledge base, and, optionally, rules-based systems with preferences associated with individual users or groups of users to generate and present images that appears as photographed anatomical slices instead of or in addition to the images generated by the imaging modality. It should be understood that although the methods and systems are described here as generating a simulated anatomical photograph (as a static image), the methods and systems may similarly be used to generate a simulated anatomical photograph as a series of images or a moves. For example, the systems and methods may generate a series of simulated anatomical photographs (a movie) that depict flowing blood in a vessel or an area of vascular blush. Similarly, the systems and methods may generate simulated anatomical photographs that are two-dimensional or three-dimensional. For example, when an imaging modality provides a three-dimensional medical image (a volume), the systems and methods may use multi-planar reconstruction software or three-dimensional simulation software to generate a simulated anatomical photograph in three-dimensions. Also, in some embodiments, the methods and systems described herein may use multiple imaging studies on the same patient to show a simulation of the entire patient's body or body part, so that a user can dynamically produce cross-sectional medical images employing a multi-planar reformatting software interface. Also, it should be understood that the SAP generated as described here can be displayed, printed (in two-dimensions or three-dimensions), or transmitted (securely) to other electronic devices.

SAPs may also be used to organize and design exam lists and timelines. For example, current PACS and other information systems provide suboptimal human interfaces for enabling doctors and other users (other healthcare workers and patients) to navigate to various medical imaging exams. These systems typically show lists of exams and associated information that can be sorted or filtered in various ways, but the systems ignore the most critical latent need of the user, which is to quickly understand what body parts a patient has had imaged and how a particular body part appears based on all available information on a particular date or dates. For example, a doctor may see a patient with headache and want to know how the brain most likely appeared in view of all available clinical and imaging data on a date such as today, a day in the past, a day in the future, the day last imaged, or a plurality of these dates. If SAPs can be generated, a user interface can be generated that no longer presents a patient's health information discretely tied to the presentation of particular imaging exams performed on particular dates.

For example, rather than providing a traditional imaging exam timeline and sortable and filterable lists, embodiments described herein can be used to generate and provide a user interface that allows a user to select and specify the generation and display of SAPs and source imaging data as well as other source information (both clinical and non-clinical information) to provide compiled diagnostic information as images.

For example, a patient may present with symptoms related to a particular body part, say the left shoulder. A user may be able to interact with the system 100 via a GUI or speech and indicate: "show me what the left shoulder most likely looks like today" or "show me what the left shoulder looked like when last imaged" or "show me what the left shoulder looks like today based on all available information" or " . . . based on only MM data" or " . . . based on my usual preferences for viewing a shoulder." As another example, a patient may present after chemotherapy for liver metastases, and may have had various CT, PT, and MRI images of his or her liver captured in January, February, April, and August and November. Instead of the user needing to view each exam and mentally synthesize the appearance and changes, the user may interact with the system 100 and indicate via a GUI or speech: "show me what the liver most likely looked like at quarterly intervals this past year" or " . . . at weekly intervals since the most recent surgical intervention" or "at monthly intervals since the last change in chemotherapy." Again, instead of being restricted to the arduous task of selecting exams of various modalities and synthesizing both imaging and clinical information, the user can simply ask for what needs to be most critically conceptualized to make management decisions. Again, as discussed above, preferences and rules may be used (and automatically generated using various artificial intelligence techniques) to control default display and default interactions. As noted above, the rules may be related to a specific user, a user role, patient attributes, a geographic location, a specialty, a disease, or the like.

For example, FIGS. 5-9 illustrate example graphical user interfaces for displaying SAPs. The example graphical user interfaces may be used in addition to or in place of a traditional PACS exam list or imaging timeline. The graphical user interface may be accessed via a patient search, launched from a third party information system (such as a HIS), a speech command, or a conversation interaction. Accordingly, although the description of the user interfaces and graphical user interfaces included in the present application are described as being drive by touch or mouse or cursor actions, other options for interacting with a user are possible, including a conversational interface.

Figure 5:
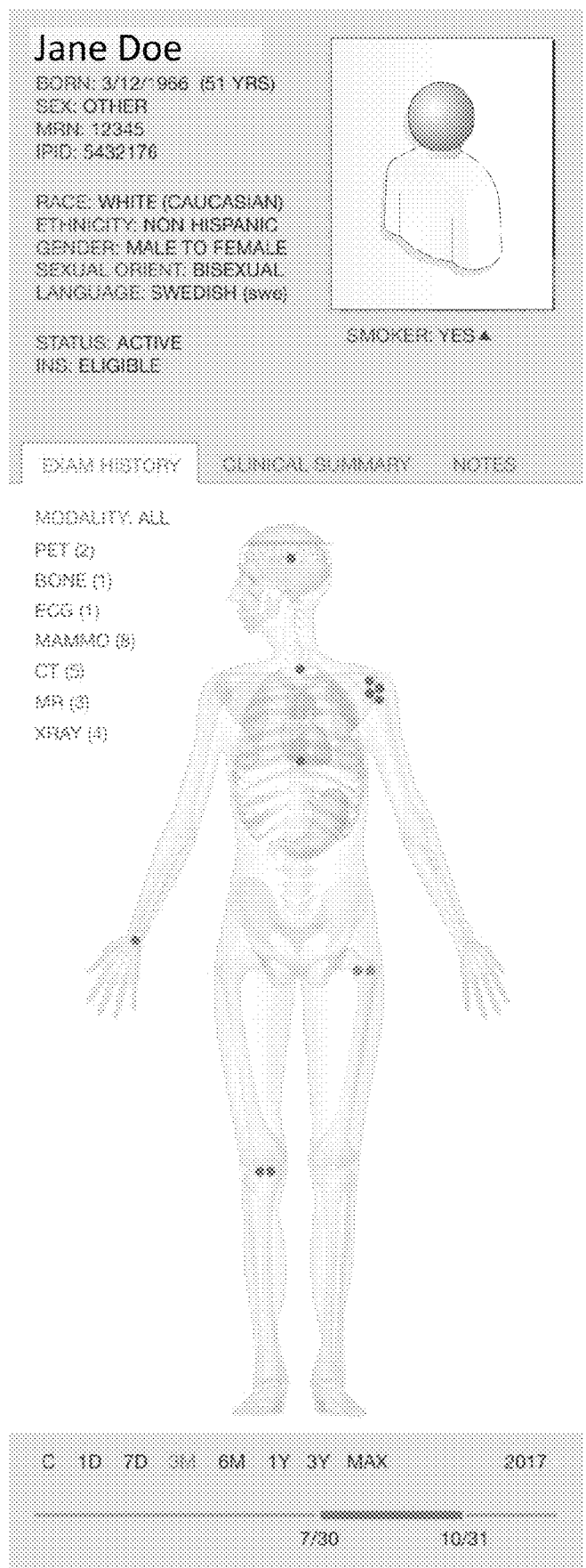
FIGS. 5-9 illustrate example graphical user interfaces for displaying simulated anatomical photographs generated by the system of FIG. 1.

As illustrated in FIG. 5, the graphical user interface displays patient demographic and personal information with optional photograph. The graphical user interface also includes a human figure representation that shows where a patient was imaged and an indication of what modalities or types of imaging information is available. The graphical user interface may also show if non-imaging information is available that contributes to the production of SAPs (such as lab, genetic, or surgical history). The graphical user interface may also include graphic indications indicating whether an exam was normal or abnormal, the modality used, an exam age, or a combination thereof. The graphical user interface also allows the user to set dates and date ranges if desired.

Figure 6:
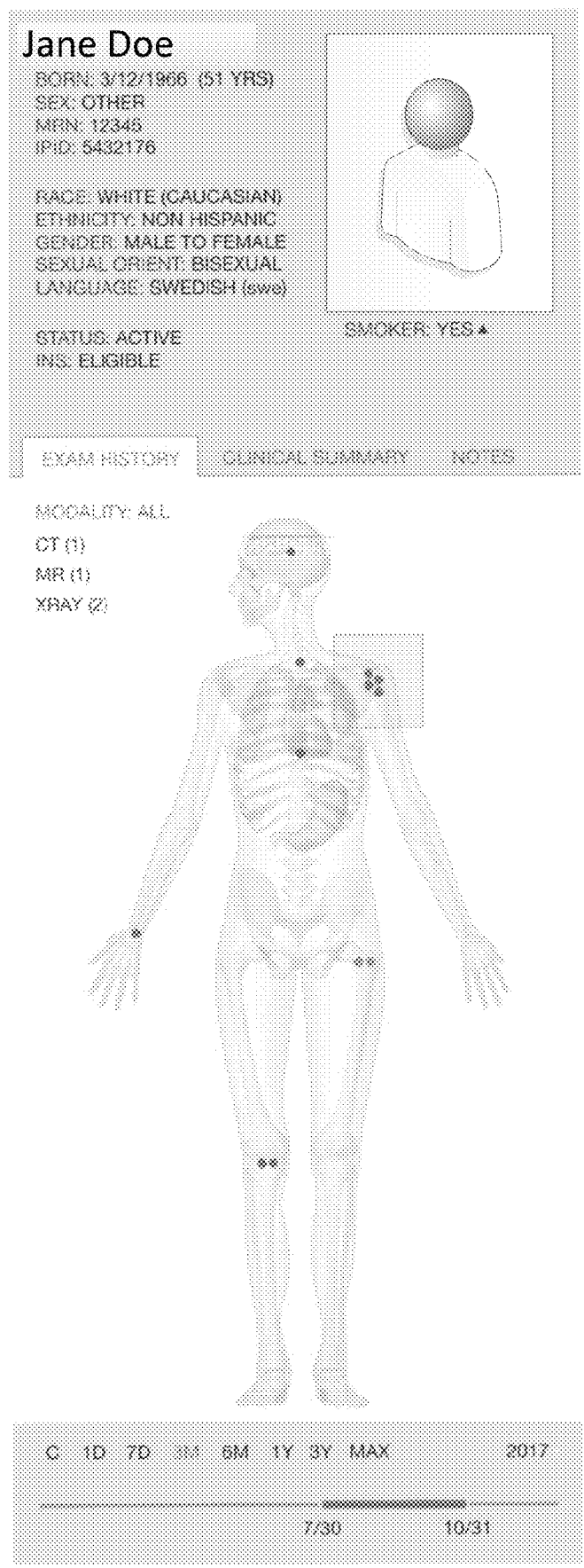
Figure 7:
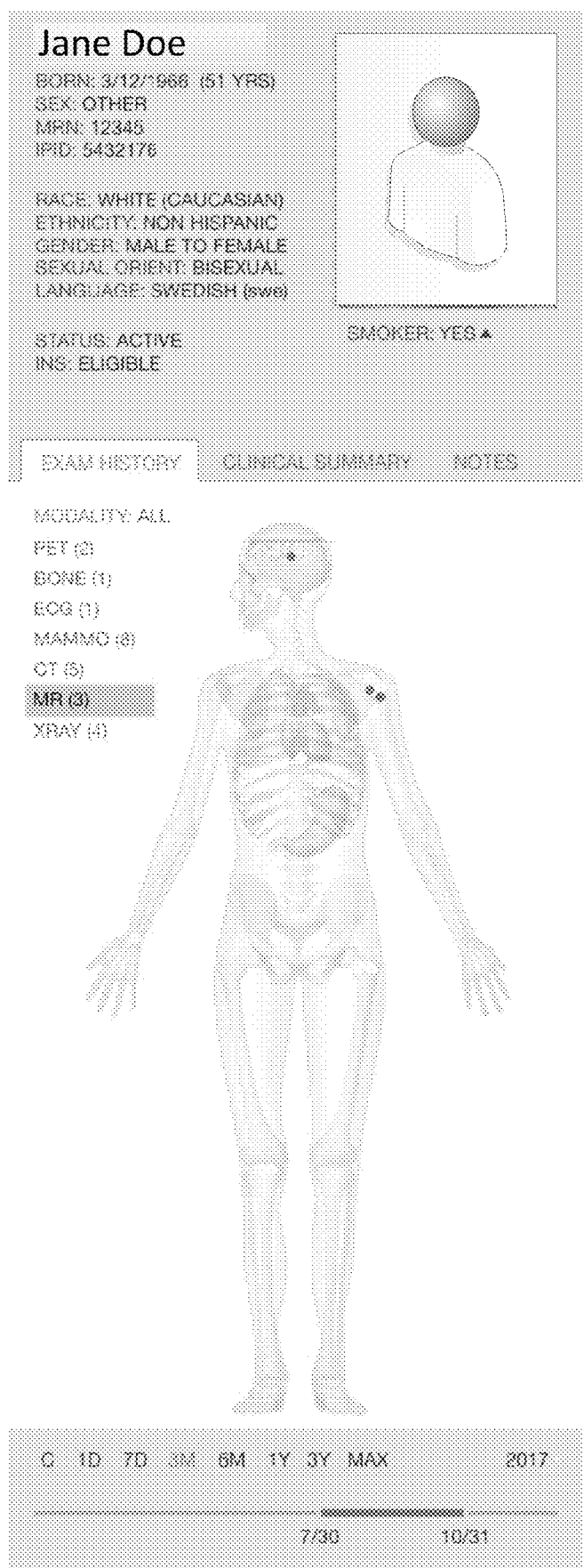

For example, as illustrated in FIGS. 6-7, in addition to setting a date, multiple dates, or a date range, the graphical user interface allows a user to indicate which imaging or non-imaging information contributes to the SAPs. For example, in FIG. 6, the user has selected the shoulder and can see which imaging exams were performed during the selected data range. Similarly, in FIG. 7, the user has indicated that only MM data is to be used to create the SAPs for the shoulder for this data range.

Figure 8:
Figure 8:
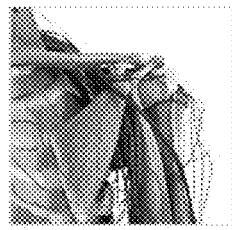
Figure 8:
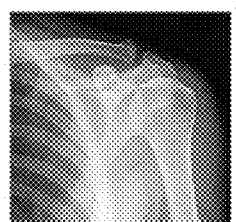
Figure 8:
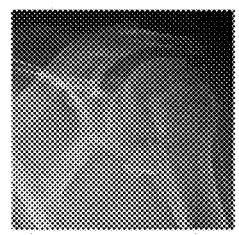
Figure 8:
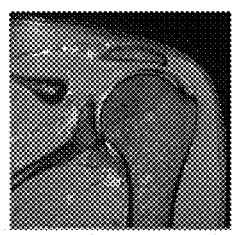
Figure 8:
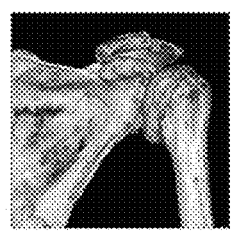

In FIG. 8, the user has selected the right shoulder and a date range. As illustrated in FIG. 8, within the graphical user interface the user can not only see a thumbnail representation of the exams that were done in the time range, but can see the predicted volumetric SAP for any date(s) or date range selected, page back through the thumbnail of each modality to see other exams of that modality performed previously, adjust the date range or date of the desired SAP or SAPs, select which imaging or clinical information contributes to the SAPs, or a combination thereof.

Figure 9:
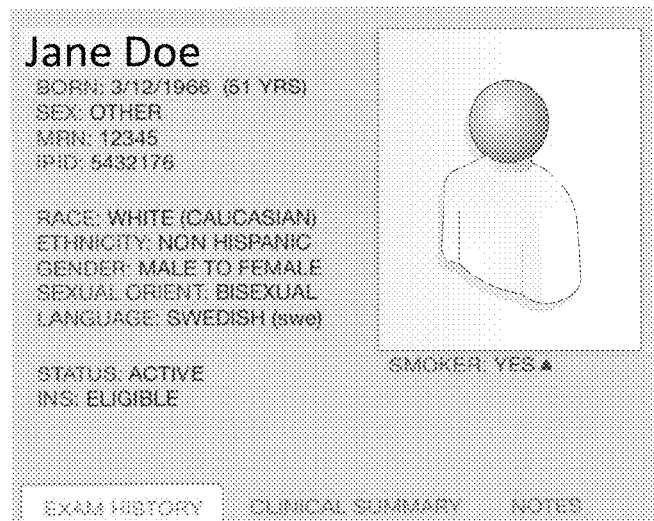
Figure 9:
Figure 9:
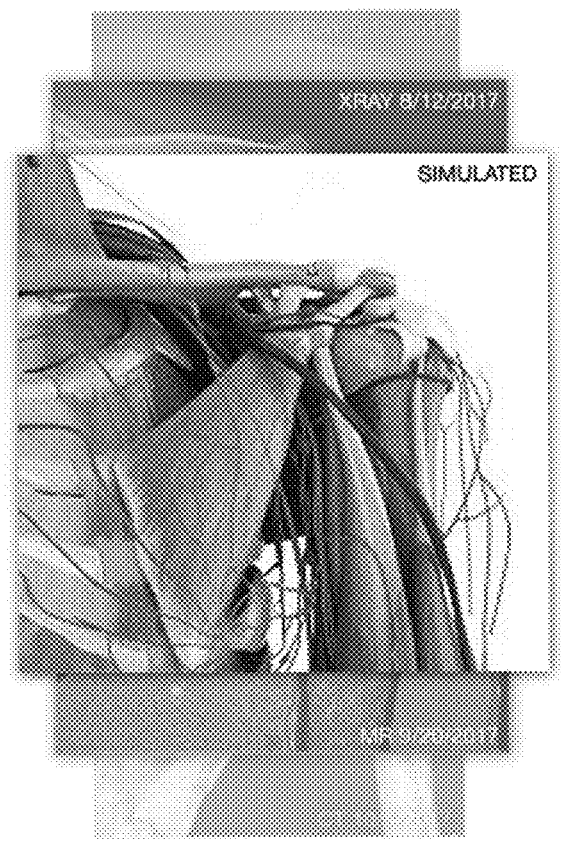

In FIG. 9, the graphical user interface displays the SAPs and the images from various exams in a virtual stack so that the user can navigate to various exams of the selected body part from various different dates. An input (mouse, audio, conversation) can control whether a user moves from SAPs to another modality or back to prior exams of a particular modality. The user can also select one or more of such exams to display in another area side by side or via some other display arrangements.

It should be understood that the graphical user interfaces illustrated in FIGS. 5-9 may be generated via the electronic processor 130 for transmission and display on the user device 115. However, in other embodiments, a dedicated viewer application executed by an electronic processor of the user device 115 may be configured to generate and display the graphical user interfaces based on data received from the server 105 (such as the SAPs). In still other embodiments, as noted above, the dedicated viewer application executed by the user device 115 may be configured to generate SAPs and perform the other processing described above as being performed by the server 105.

Regardless of what device performs the functionality, the graphical user interface allows a user to specify first selection designating a body part of a patient and designate a second selection designating a time period (a date, a plurality of dates, a date range, or the like). As described above, in some embodiments, the graphical user interface includes a graphical representation of body, wherein portions of the graphical representation are selectable (for example, the knee, liver, lungs, and the like) to select the relevant body part. The graphical representation may also include one or more indications that mark body parts associated with available imaging exams for the patient. The indication may specify (via color, shape, animation, symbol, or the like) the imaging modality used to generate the imaging exam, a finding of the imaging exam (for example, normal or abnormal), an exam age, or a combination thereof.

Based on the first and second selections, imaging and optionally non-imaging information for the patient is automatically accessed and the accessed information is used to automatically generate a SAP for the selected body part at the selected time period. As noted above, the generated SAP represents a likely appearance of the selected body part at the selected time period, wherein the selected time period may be different than any available imaging exam for the patient. As noted above, the imaging information accessed for a patient may include imaging exams generated for the selected body part at time periods different than the received time period, imaging exams generated by the same or different imaging modalities or imaging procedures, or the like. The non-imaging information may include lab results, genetic information, surgical results, treatment information, and the like. Also, in some embodiments, non-clinical information is also accessed and used to generate the SAP. The non-clinical information may include research or clinical information not specifically associated with the patient, community information, and the like.

The generated SAP is then displayed within the graphical user interface. In some embodiments, the graphical user interface displays the SAP and one or more source medical images accessed as part of the imaging information. As noted above, the SAP and the source medical images may be displayed in a virtual stack, which may be organized chronologically and allows a user to navigate through both actual medical images of the patient and SAPs.

In some embodiments, the user may be able to set various preferences for how SAPs are generated and displayed. For example, as described above, a user may be able to selection what types of imaging exams should be used or excluded when generating a SAP. The user may also be able to specify whether a SAP is displayed with source medical images, whether and what non-imaging information should be used, whether and what non-clinical information should be used, and the like. These rules or preferences may be configurable through the graphical user interface. Alternatively or in addition, these rules or preferences may be automatically generated using machine learning as described above. In some embodiments, the reading physician's understanding of the images and resultant report can also be used to modify the appearance of a SAP. In other words, as a doctor dictates a report, that information can be captured via natural language processing (NLP) or a conversational interface and used to create or modify a SAP. For example, a doctor may say, "Given all available clinical and imaging factors and taking into account the X-rays, MRIs and CTs, the most likely diagnosis in the left thigh is a malignant fibrous histiocytoma." In response, the system 100 may be configured to automatically modify its SAP options (such as by setting a particular SAP as the "most likely SAP" using this additional piece of data. Similarly, if a doctor indicates that a particular piece of anatomy includes a tumor, a fat deposit, or the like, the system 100 may be configured to automatically update a previously-generated SAP to convey this description. Accordingly, a description from a physician may be used to create a better picture of what is in the physician's imagination, and, when implemented in a real-time environment, a physician can see what his or her words are actually describing in image form, which may also allow the physician to change his or her words to draw a better a picture. Thus, the system may be configured to initially create or modify a previously-created SAP in response to (dictated) diagnoses or descriptions from a physician, such as diagnoses and descriptions added to a physician's report. The system 100 may also provide the reading physician with a SAP modified as a result of the reading physician's report so that the reading physician can see what he or she is describing and, if desired or necessary, make further modifications or edits to the description to subsequently modify the SAP.

Various features and advantages of the invention are set forth in the following claims.

What is claimed is:

1. A system for generating and displaying a simulated anatomical photograph, the system comprising:
   an electronic processor configured to
      receive a first selection from a user, the first selection designating a body part of a patient,
      receive a second selection from the user, the second selection designating a time period,
      automatically access imaging information for the patient associated with the first selection and the second selection,
      automatically generate the simulated anatomical photograph for the body part for the time period based on the imaging information, and
      display the simulated anatomical photograph to the user within a graphical user interface.

2. The system of claim 1, wherein the electronic processor is configured to receive at least one of the first selection and the second selection through the graphical user interface, the graphical user interface including a graphical representation of a body including selectable portions.

3. The system of claim 2, wherein the graphical representation of the body includes at least one indication marking a body part within the graphical representation associated with an imaging exam for the patient.

4. The system of claim 3, wherein the at least one indication identifies at least one selected from a group consisting of a type of the imaging exam for the patient, a finding of the imaging exam for the patient, and an age of the imaging exam for the patient.

5. The system of claim 1, wherein the electronic processor is further configured to automatically modify the simulated anatomical photograph in response to a description included in a report associated with the imaging information and display the simulated anatomical photograph as modified to a physician providing the description.

6. The system of claim 1, wherein the electronic processor is configured to receive at least one of the first selection and the second selection through a speech command.

7. The system of claim 1, wherein the time period includes a date.

8. The system of claim 1, wherein the time period includes a plurality of dates.

9. The system of claim 1, wherein the time period includes a date and wherein the imaging information includes at least one imaging exam generated on a different date.

10. The system of claim 1, wherein the imaging information includes a plurality of imaging exams of the body part.

11. The system of claim 10, wherein the plurality of imaging exams of the body part include at least two imaging exams generated by different imaging modalities.

12. The system of claim 10, wherein the plurality of imaging exams of the body part include at least two imaging exams generated by different imaging procedures.

13. The system of claim 1, wherein the electronic processor is further configured to automatically access non-imaging information for the patient associated with the first selection and the second selection and wherein the electronic processor is configured to automatically generate the simulated anatomical photograph for the body part as of the time period based on the imaging information and the non-imaging information.

14. The system of claim 1, wherein the electronic processor is further configure to display at least one source medical image accessed as part of the imaging information within the graphical user interface.

15. The system of claim 14, wherein the electronic processor is configured to display the at least one source medical image within the graphical user interface in a virtual stack with the simulated anatomical photograph, wherein the virtual stack is organized chronologically.

16. The system of claim 1, wherein the electronic processor is configured to automatically generate the simulated anatomical photograph based on at least one user preference.

17. The system of claim 16, wherein the electronic processor is configured to automatically generate the at least one user preference using machine learning.

18. The system of claim 1, wherein the electronic processor is further configured to receive a third selection indicating at least one type of imaging exam included in the imaging information to use to generate the simulated anatomical photograph or at least one type of imaging exam included in the imaging information to exclude to generate the simulated anatomical photograph.

19. A method of generating and displaying a simulated anatomical photograph, the method comprising:
receiving, with an electronic processor, a first selection from a user within a graphical user interface, the first selection designating a body part of a patient by selecting a selectable portion of a graphical representation of a body included in the graphical user interface;
receiving, with the electronic processor, a second selection from the user, the second selection designating a time period;
automatically accessing, with the electronic processor, imaging information for the patient associated with the first selection and the second selection;
automatically generating, with the electronic processor, the simulated anatomical photograph for the body part for the time period based on the imaging information, wherein the simulated anatomical photograph estimates an appearance of the body part for the time period in a cross-sectional anatomical slice; and
displaying the simulated anatomical photograph to the user within the graphical user interface.

20. Non-transitory computer-readable medium storing instructions that, when executed with an electronic processor, perform a set of functions, the set of functions comprising:
receiving a first selection from a user, the first selection designating a body part of a patient;
receiving a second selection from the user, the second selection designating a time period;
automatically accessing imaging information for the patient associated with the first selection and the second selection and non-imaging information for the patient associated with the first selection and the second selection;
automatically generating a simulated anatomical photograph for the body part for the time period based on the imaging information and non-imaging information, wherein the simulated anatomical photograph estimates an appearance of the body part for the time period in a cross-sectional anatomical slice; and
displaying the simulated anatomical photograph to the user within the graphical user interface.

* * * * *